(12) United States Patent
Lamont et al.

(10) Patent No.: US 9,782,599 B2
(45) Date of Patent: *Oct. 10, 2017

(54) POWER ARCHITECTURE FOR AN IMPLANTABLE MEDICAL DEVICE HAVING A NON-RECHARGEABLE BATTERY

(71) Applicant: Boston Scientific Neuromodulation Corporation, Valencia, CA (US)

(72) Inventors: Robert G. Lamont, Van Nuys, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/431,284

(22) Filed: Feb. 13, 2017

(65) Prior Publication Data

US 2017/0165492 A1 Jun. 15, 2017

Related U.S. Application Data

(63) Continuation of application No. 15/166,523, filed on May 27, 2016, now Pat. No. 9,579,513, which is a (Continued)

(51) Int. Cl.
*A61N 1/36* (2006.01)
*A61N 1/378* (2006.01)
(Continued)

(52) U.S. Cl.
CPC .............. *A61N 1/378* (2013.01); *A61N 1/025* (2013.01); *A61N 1/04* (2013.01); *A61N 1/08* (2013.01)

(58) Field of Classification Search
CPC .. A61N 1/36125; A61N 1/36128; A61N 1/37; A61N 1/3706; A61N 1/3708; A61N 1/378; A61N 1/3782
See application file for complete search history.

(56) References Cited

U.S. PATENT DOCUMENTS 5,757,167 A * 5/1998 Arora .................... H02J 7/0065
323/224
6,076,018 A 6/2000 Sturman et al.
(Continued)

OTHER PUBLICATIONS

International Search Report and Written Opinion regarding application No. PCT/US2013/023890 dated Apr. 24, 2013.

*Primary Examiner* — George Evanisko
(74) *Attorney, Agent, or Firm* — Lewis, Reese & Nesmith, PLLC (57) ABSTRACT

An improved architecture for an implantable medical device using a primary battery is disclosed which reduces the circumstances in which the voltage of the primary battery is boosted, and hence reduces the power draw in the implant. The architecture includes a boost converter for selectively boosting the voltage of the primary battery and for supplying that boosted voltage to certain of the circuit blocks, including digital circuitry, analog circuitry, and memory. However, the boost converter is only used to boost the battery voltage when its magnitude is below a threshold; if above the threshold, the battery voltage is passed to the circuit blocks without boosting. Additionally, some circuitry capable of operation even at low battery voltages—including the telemetry tank circuitry and the compliance voltage generator—receives the battery voltage directly without boosting, and without regard to the current magnitude of the battery voltage.

20 Claims, 5 Drawing Sheets

Related U.S. Application Data continuation of application No. 13/747,898, filed on Jan. 23, 2013, now Pat. No. 9,352,162.

(60) Provisional application No. 61/597,250, filed on Feb. 10, 2012.

(51) Int. Cl.
  *A61N 1/02* (2006.01)
  *A61N 1/04* (2006.01)
  *A61N 1/08* (2006.01)

(56) References Cited

U.S. PATENT DOCUMENTS

| | | |
|---|---|---|
| 6,094,597 A | 7/2000 | Wold |
| 6,154,374 A | 11/2000 | Uejima et al. |
| 6,289,246 B1 | 9/2001 | Money |
| 6,567,703 B1 | 5/2003 | Thompson et al. |
| 7,024,246 B2 | 4/2006 | Acosta et al. |
| 7,711,419 B2 | 5/2010 | Armstrong et al. |
| 7,872,884 B2 | 1/2011 | Parramon et al. |
| 8,442,643 B2 | 5/2013 | Toy et al. |
| 8,463,390 B2 | 6/2013 | Muraoka |
| 2007/0097719 A1* | 5/2007 | Parramon .............. A61N 1/378 363/72 |
| 2008/0319497 A1 | 12/2008 | Griffith et al. |
| 2009/0069869 A1 | 3/2009 | Stouffer et al. |
| 2010/0010559 A1 | 1/2010 | Zhang et al. |
| 2010/0211132 A1 | 8/2010 | Nimmagadda et al. |
| 2010/0231175 A1 | 9/2010 | Noda |
| 2011/0276110 A1 | 11/2011 | Whitehurst et al. |
| 2012/0095744 A1 | 4/2012 | Rahman et al. |
| 2012/0172948 A1 | 7/2012 | Aghassian et al. |
| 2013/0023943 A1 | 1/2013 | Parramon et al. |

\* cited by examiner

POWER ARCHITECTURE FOR AN IMPLANTABLE MEDICAL DEVICE HAVING A NON-RECHARGEABLE BATTERY

CROSS-REFERENCE TO RELATED APPLICATIONS

This is a continuation of U.S. patent application Ser. No. 15/166,523, filed May 27, 2016, which is a continuation of U.S. patent application Ser. No. 13/747,898, filed Jan. 23, 2013 (U.S. Pat. No. 9,352,162), which is a Non-Provisional of U.S. Provisional Patent Application Ser. No. 61/597,250, filed Feb. 10, 2012. Priority is claimed to these applications, and they are incorporated herein by reference in their entireties.

FIELD OF THE INVENTION

The present invention relates generally to implantable medical devices, and more particularly to improved architectures for an implantable medical device having a primary battery.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device.

Figures 1A, 1B:
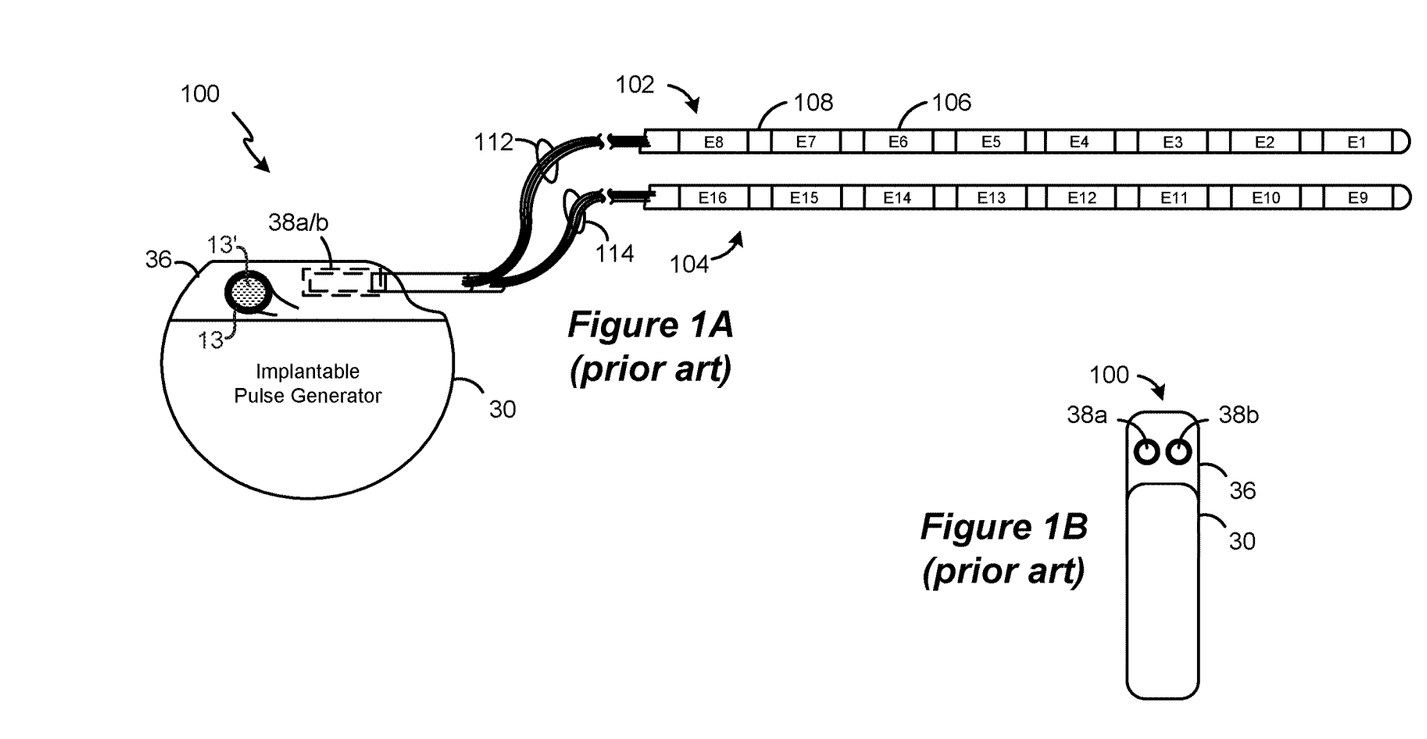
FIGS. 1A and 1B show an implantable pulse generator (IPG), and the manner in which an electrode array is coupled to the IPG in accordance with the prior art.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry of the IPG and a battery to provide power to the circuitry. Depending on the particular needs and circumstances of the patient who will be using the IPG, the battery can be either rechargeable or a non-rechargeable primary battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are eight electrodes on array 102, labeled $E_1$-$E_8$, and eight electrodes on array 104, labeled $E_9$-$E_{16}$, although the number of arrays and electrodes is application specific and therefore can vary. The arrays 102, 104 couple to the IPG 100 using lead connectors 38a and 38b, which are fixed in a non-conductive header material 36, which can comprise an epoxy for example.

Figure 2:
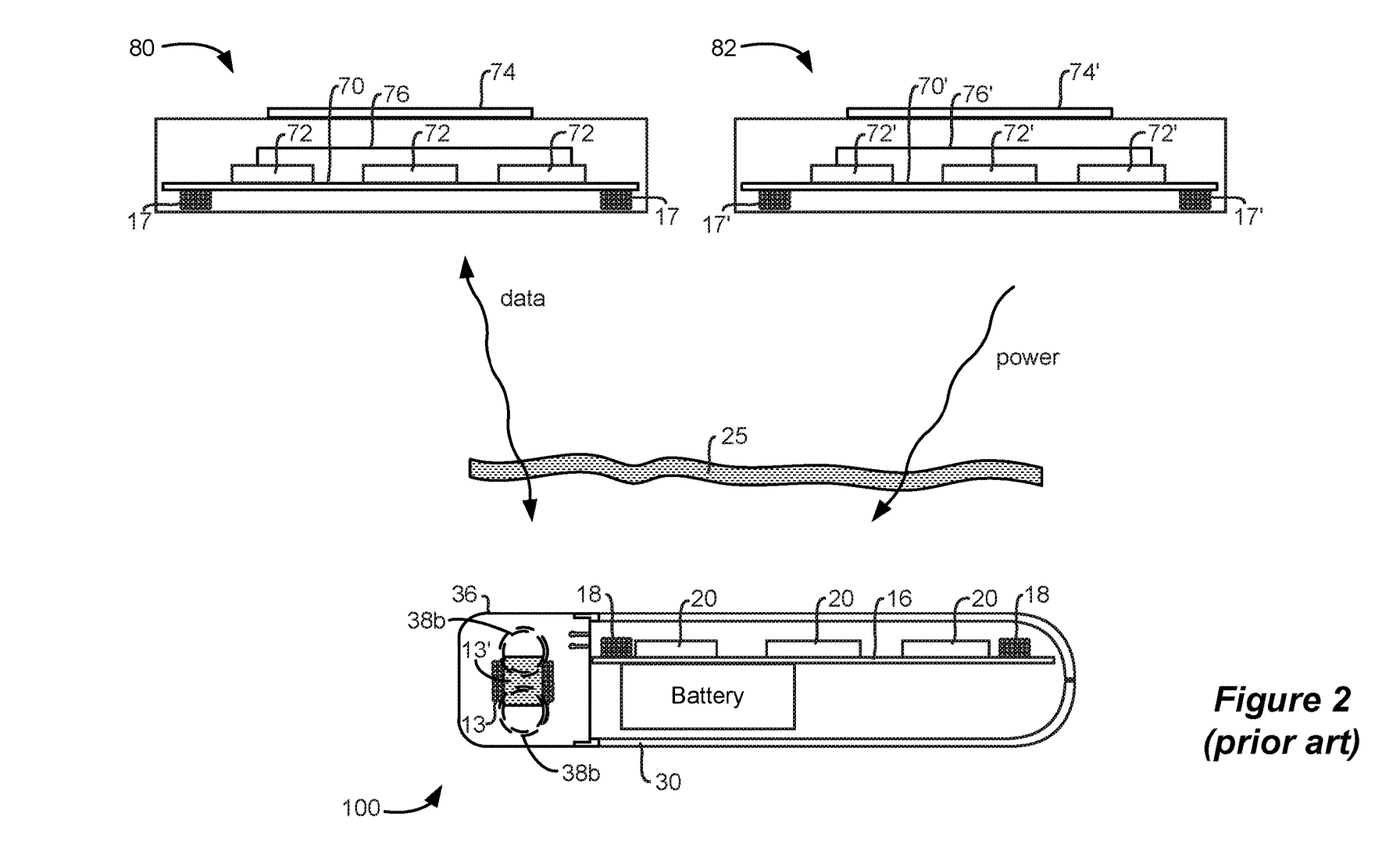
FIG. 2 illustrates an IPG, an external controller, and an external charger in accordance with the prior art.

As shown in FIG. 2, the IPG 100 typically includes an electronic substrate assembly including a printed circuit board (PCB) 16, along with various electronic components 20, such as microprocessors, integrated circuits, and capacitors mounted on the PCB 16. Some of these electronic components 20 are discussed further below. A telemetry coil 13 (more generally, an antenna) is generally present in the IPG 100 to transmit/receive data to/from an external controller 80. The telemetry coil 13 is typically mounted within the header 36 of the IPG 100 as shown, and may be wrapped around a ferrite core 13'. In other embodiments, the telemetry coil 13 may be within the case 30. In an IPG having a rechargeable battery, such as the IPG 100, a charging coil 18 is also present for charging or recharging the IPG's battery using an external charger 82.

As just noted, an external controller 80, such as a hand-held programmer or a clinician's programmer, is used to wirelessly send data to and receive data from the IPG 100. For example, the external controller 80 can send programming data to the IPG 100 to dictate the therapy the IPG 100 will provide to the patient. Also, the external controller 80 can act as a receiver of data from the IPG 100, such as various data reporting on the IPG's status. The external controller 80, like the IPG 100, also contains a PCB 70 on which electronic components 72 are placed to control operation of the external controller 80. A user interface 74 similar to that used for a computer, cell phone, or other hand held electronic device, and including touchable buttons and a display for example, allows a patient or clinician to operate the external controller 80. The communication of data to and from the external controller 80 is enabled by a coil (antenna) 17, which communicates with coil 13 in the IPG 100.

The external charger 82, also typically a hand-held device, is used to wirelessly convey power to the IPG 100, which power can be used to recharge the IPG's battery if it is rechargeable. The transfer of power from the external charger 82 is enabled by a coil (antenna) 17', which generates power received by coil 18 in the IPG 100. The external charger 82 is depicted as having a similar construction to the external controller 80, but in reality they will differ in accordance with their functionalities as one skilled in the art will appreciate.

Figure 3:
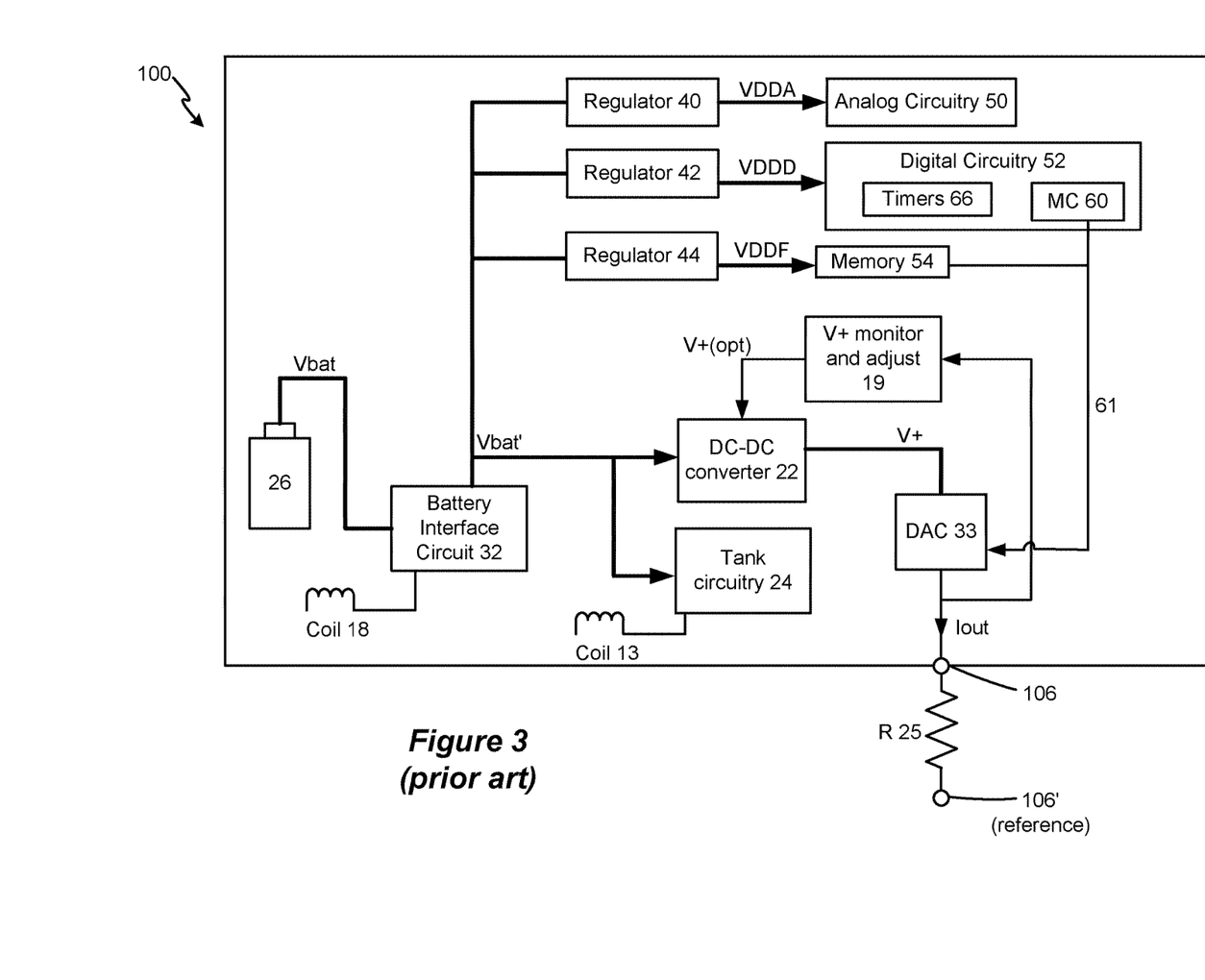
FIG. 3 illustrates aspects of an IPG power architecture using a rechargeable battery in accordance with the prior art.

FIG. 3 illustrates an architecture for an IPG 100 that uses a rechargeable battery 26. Shown with particular emphasis in FIG. 3 are the various power supplies in the IPG 100, which are the focus of this disclosure and which are shown with thicker lines. Only a few other non-power supply signals are shown in FIG. 3 to the extent they are discussed below, and such signals are shown with thinner lines. One skilled in the art will appreciate that the IPG 100 contains many such "regular" signal lines, which are not shown for convenience.

Rechargeable battery 26 typically comprises a Lithium ion polymer battery, and depending on its level of depletion can have a battery voltage, Vbat, of about 3.2 to 4.2 Volts. The IPG 100 includes a battery interface circuit 32, which acts as an intermediary between the charging coil 18 and the rechargeable battery 26. The battery interface circuit 32 contains circuitry for rectifying power received at the charging coil 18 from the external charger 82 (FIG. 2) and for charging the rechargeable battery 26 in a controlled fashion. Power from the rechargeable battery 26 is routed through controllable switching circuitry in the battery interface circuit 32 and supplied to the rest of the circuitry in the IPG 100 as voltage, Vbat'. The magnitude of Vbat' is essentially the same as Vbat, minus a small voltage drop that occurs across the switching circuitry in the battery interface circuit 32. Examples of battery interface circuitry 32 can be found in U.S. Patent Application Publication 2013/0023943.

The battery interface circuit 32 supplies the voltage Vbat' to various circuit elements in the IPG 100 via voltage regulators 40, 42, and 44. The regulators 40, 42, and 44 are used to regulate Vbat' to power supply voltages VDDA, VDDD, and VDDF appropriate to power the circuit elements to which they are connected, i.e., analog circuitry 50, digital circuitry 52, and memory 54 respectively. The regulators 40, 42, and 44 can comprise low power, low drop out linear regulators that use very little power, which is particularly useful in a battery powered implanted medical device as it conserves power. Linear regulators are also advantageous because they create less noise than switching regulators.

Although the magnitude of the power supply voltages VDDD, VDDA, VDDF needed for each of circuitries 50, 52, and 54 may be the same, each circuitry is preferably supplied power by its own voltage regulator. The analog circuitry 50 and the digital circuitry 52 preferably have separate regulators 40 and 42 because the digital circuitry 52 creates noise on VDDD as it switches, which noise could potentially affect the performance of the analog circuitry 50. Memory 50 preferably has its own regulator 44 because the memory 50 may consume a large amount of current, which VDDF must supply. Additionally, VDDF can be shut down from time to time to save power.

Analog circuitry 50 contains a number of low voltage analog circuitry elements within the IPG 100 that are powered by power supply VDDA, including thermistors, band gap voltage references, oscillators and clocks, modulation and demodulation circuitry that send data to and receives data from the tank circuitry 24 coupled to the telemetry coil 13, analog measurement and routing circuitry, and the like. VDDA in one example may comprise 2.8 Volts.

Digital circuitry 52 comprises the digital circuits in the IPG 100 that are powered by power supply VDDD, including microcontroller 60 and timing circuitry 66. VDDD in one example may comprise 2.8 Volts. Digital circuitry 52 can be integrated, at least in part, on a single mixed-mode ASIC integrated circuit with at least some of the analog circuitry 50, as shown for example in U.S. Patent Publication 2008/0319497, or can be discrete therefrom.

Memory 54, which is powered by power supply VDDF, can hold the operating software for the system (e.g., for the microcontroller 60), and can also act as a free space to store data, such as logged data to be reported to the external controller 80 for analysis and/or feedback to the patient. Memory 54 can also store data transmitted from the external controller 80, such as the therapy setting referred to earlier, which data can in turn be sent to the microcontroller 60. Memory 54 may be any type of memory, such as Flash EPROM, random access memory (RAM), static RAM (SRAM), a hard drive, or the like. However, to ensure data retention even when power is lost, memory 54 often comprises a Flash EPROM memory. Because a Flash EPROM can require additional current to both program and erase, VDDF is typically provided by a higher-powered regulator 44, as mentioned previously. VDDF in one example may comprise 2.8 Volts.

Rechargeable battery 26 also provides the power necessary to send therapeutic current pulses through particular stimulating electrodes 106. This is done by producing a compliance voltage, V+, using a DC-DC converter 22. Converter 22, like regulators 40, 42, and 44, creates a voltage (V+) from Vbat', which is used to power one or more Digital-to-Analog Converters (DAC) 33 to produce therapeutic current, Iout. The compliance voltage V+in effect comprises the power supply for the DAC(s) 33. The magnitude of the therapeutic current, Iout, produced by the DAC(s) 33 is specified by digital signals 61. Iout is output to a particular electrode 106 of the IPG 100, which may be selected, where it passes through the tissue, R 25, of the patient. (Another electrode 106' can provide a return path, or reference, for Iout).

Because the therapeutic current can vary from time to time, the compliance voltage V+ necessary to produce this current can vary as well, and thus V+ can be changed by the converter 22. As explained in U.S. Patent Publication 2007/0097719, V+ monitor and adjust circuitry 19 can measure the voltage at the electrode 106 when the DAC 33 is issuing the therapeutic current, and can inform the converter 22 of a value for V+, V+(opt), that is optimal to supply that current. As explained in the '719 Publication, if V+ is too low, the DAC 33 will become "loaded" and unable to provide the desired current, Iout. If V+ is too high, the DAC 33 will be able to provide the desired current, but power will be wasted: some portion of the compliance voltage V+ will be dropped across the DAC 33 without any useful effect. As also disclosed in the '719 Publication, the converter 22 can comprise a capacitor-based change pump, an inductor-based step-up converter, or combination of these. V+ may be set by the converter 22 in one example from anywhere between 3 to 18 Volts.

Tank circuitry 24, which is coupled to the telemetry coil 13, is also powered by Vbat'. As shown in U.S. Patent Publication U.S. 2009/0069869 for example, tank circuitry 24 can comprise a tuning capacitor which operates in conjunction with the inductance of the coil 13 to set its resonant frequency, and can further include transistors controlled by modulation circuitry (part of the analog circuitry 50) to switch the tank at the resonant frequency when the coil 13 is transmitting. When receiving data, the tank circuitry 24 is instead coupled to demodulation circuitry (which may also include part of the analog circuitry 50).

Although many IPGs use rechargeable batteries, there are situations in which use of a primary battery may be advantageous. A primary battery is one in which the electrochemical reaction is not reversible by passing a charging current therethrough, thus rendering the battery non-rechargeable. Primary batteries use up the materials in one or both of their electrodes and thus have a limited life span.

Primary batteries, however, are typically cheaper than rechargeable batteries, and may not suffer from the same reliability concerns. As such, the use of primary batteries in a medical implantable device is preferred when appropriate, for example, when the expected life of the primary battery would be expected to exceed the patient's life expectancy, or in situations where patients with physical or mental limitations would have difficulty charging the battery. Using a primary battery in an implantable medical device also simplifies design, in particular because a charging coil 18 is not necessary.

Figure 4:
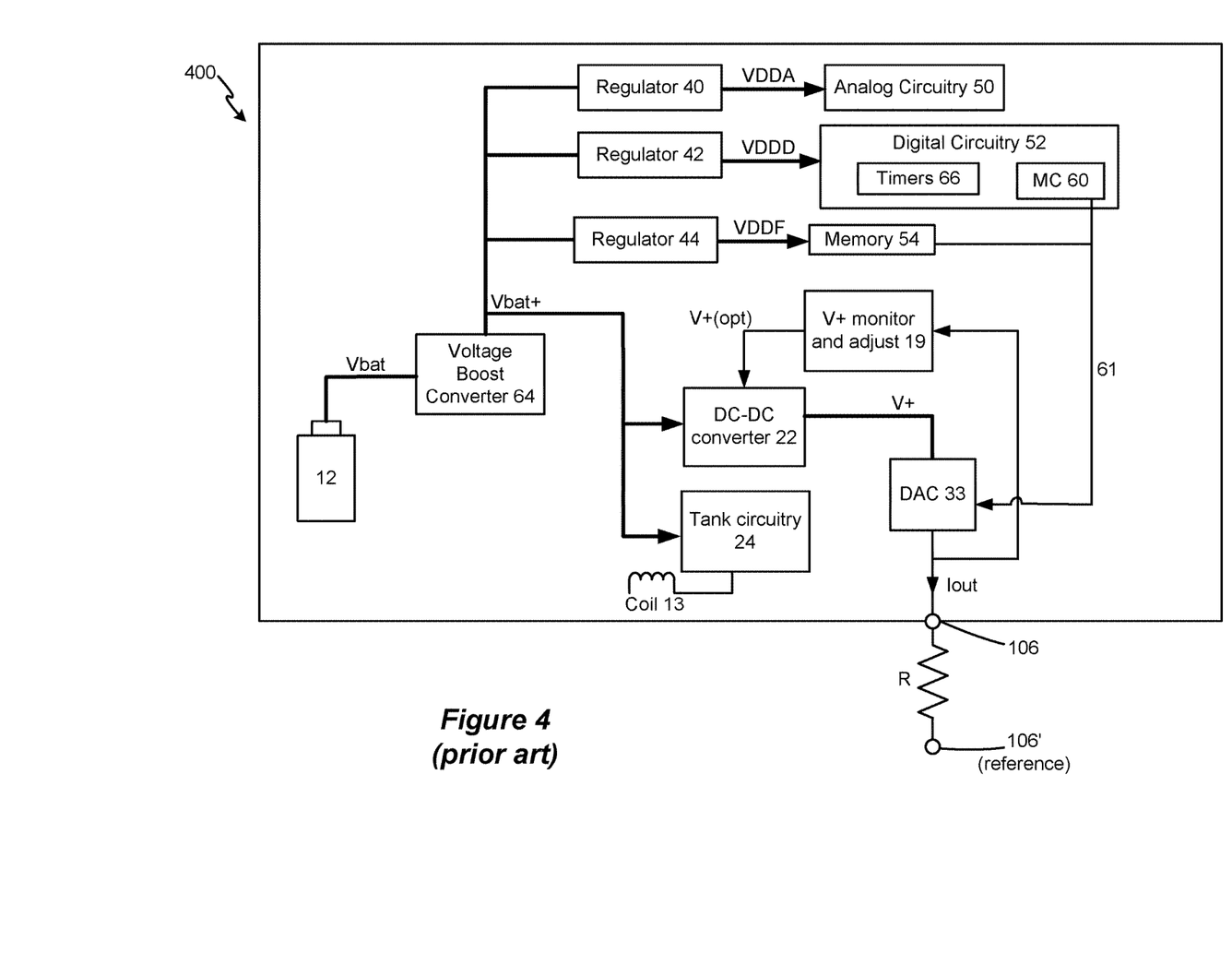
FIG. 4 illustrates aspects of an IPG power architecture using a primary battery in accordance with the prior art.

FIG. 4 illustrates an architecture for an IPG 400 using a primary battery 12, which may for example be a Lithium CFx battery or SVO hybrid with CFx having a voltage, Vbat, of 1.2 to 3.2 Volts. As shown, many of the circuit elements and connections in IPG 400 are the same as those used in the rechargeable-battery IPG 100 of FIG. 3. Such similar aspects are not again discussed.

A significant difference in the primary-battery architecture of FIG. 4 is the use of a boost converter 64 in lieu of battery interface circuit 32 to supply various circuit blocks with power from the primary battery 12. As its name implies, the boost converter 64 boosts the battery voltage, Vbat, to a higher magnitude, Vbat+, suitable for use by the circuit blocks to which it is connected—the regulators 40, 42, 44, the DC-DC converter 22, and the tank circuitry 24 coupled to the telemetry coil 13. Vbat+ in this example may be 3.2

V or so. Such boosting is necessary because of the relatively low voltage of the primary battery 12 relative to the rechargeable battery 26. If not boosted, Vbat would be too low to enable the regulators 40, 42, and 44 to produce power supply voltages VDDD, VDDA, and VDDF of the desired magnitudes (again, about 2.8V). Boost converter 64, like the DC-DC converter 22, can comprise a capacitor-based change pump, an inductor-based step-up converter, or combination of these.

Unfortunately, using a boost converter 64 to boost the voltage supplied to the circuit elements in IPG 400 is inefficient, because such boosting itself takes power from the primary battery 12. Efficiency is particularly important in an implantable medical device with a primary battery, because the primary battery cannot be recharged.

Accordingly, implantable medical devices, and more specifically implantable stimulator devices, would benefit from improved architectures that use primary batteries, and embodiments of such a solution are provided herein.

DETAILED DESCRIPTION

An improved architecture for an implantable medical device using a primary battery is disclosed which reduces the circumstances in which the voltage of the primary battery is boosted, and hence reduces the power draw in the implant. The architecture includes a boost converter for selectively boosting the voltage of the primary battery and for supplying that boosted voltage to certain of the circuit blocks, including digital circuitry, analog circuitry, and memory. However, the boost converter is only used to boost the battery voltage when its magnitude is below a threshold; if above the threshold, the battery voltage is passed to the circuit blocks without boosting. Additionally, some circuitry capable of operation even at low battery voltages—including the telemetry tank circuitry and the compliance voltage generator—receives the battery voltage directly without boosting, and without regard to the current magnitude of the battery voltage.

Figure 5:
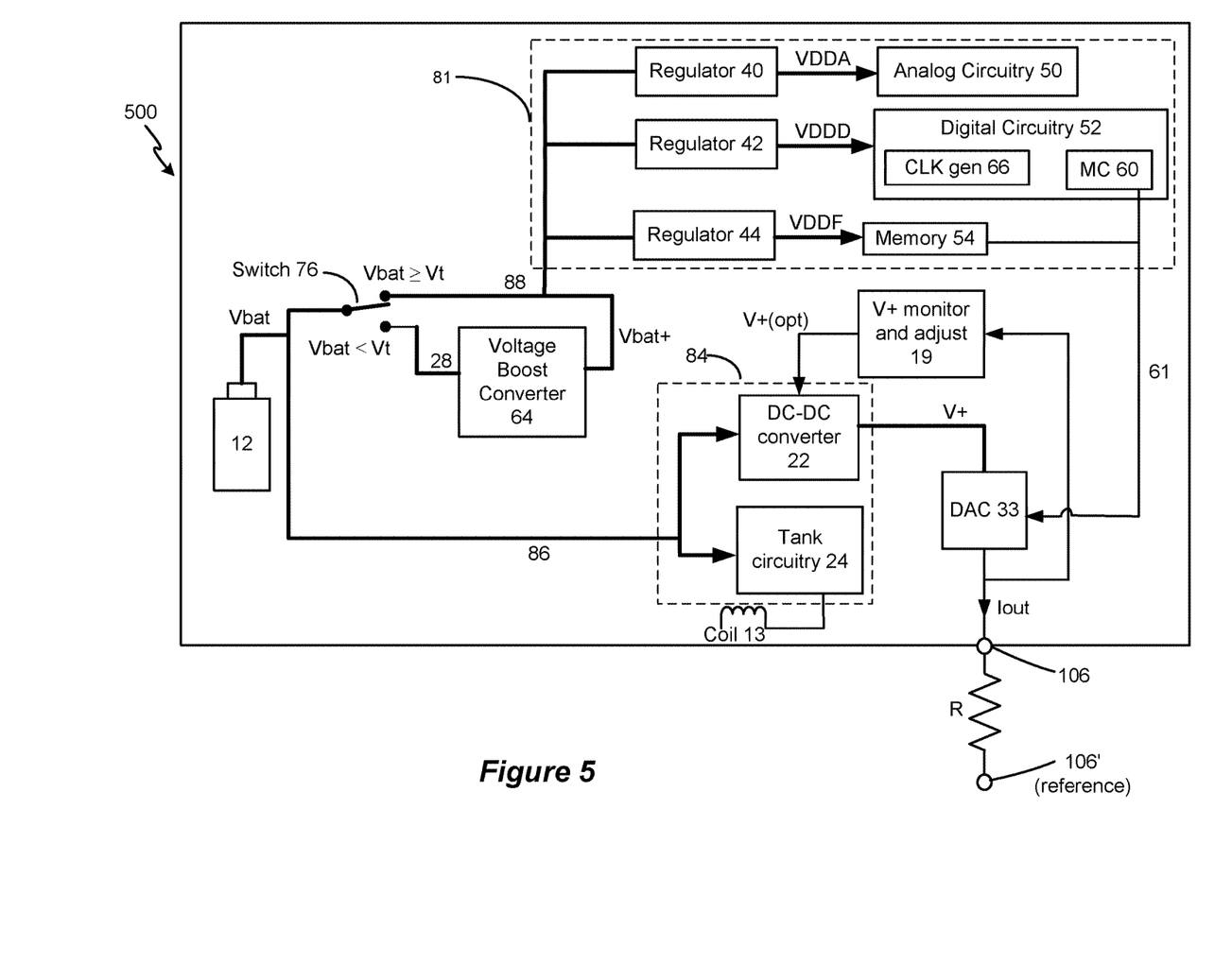
FIG. 5 illustrates aspects of an improved IPG power architecture using a primary battery.

FIG. 5 illustrates the improved architecture for an IPG 500 using a primary battery 12, which may be similar to primary batteries discussed earlier with reference to FIG. 4. Once again, many of the circuit elements and connections in IPG 500 are the same as those used in the rechargeable-battery IPG 100 of FIG. 3, and the primary-battery IPG 400 of FIG. 4. Such similar aspects are not again discussed.

As with the primary-battery architecture of IPG 400 in FIG. 4, IPG 500 comprises a boost converter 64 to potentially boost the voltage of the primary battery 12, Vbat, to a higher voltage, Vbat+, necessary to power the various circuits. However, two differences are apparent.

First, the boost converter 64 is controlled by a switch 76, which switch is set depending on Vbat's relationship to a threshold, Vt. If Vbat is greater than or equal to the threshold, the switch 76 is set to route Vbat directly to as the input power supply 88 to first circuitry 81 which includes the regulators 40, 42, and 44 that produce the power supply voltages VDDD, VDDA, and VDDF for the analog circuitry 50, the digital circuitry 52, and the memory 54 respectively. If Vbat is less than Vt, the switch 76 routes Vbat to the input 28 of the boost converter 64, thus allowing the boost converter 64 to supply a higher voltage, Vbat+, as the input power supply 88 to the first circuitry 81 and thus to the regulators 40, 42, and 44. Although not shown, the boost converter 64 can also be selectively enabled only when Vbat<Vt so that it does not attempt to boost when the switch 76 does not route Vbat to it. Such enable signal to the boost converter can comprise the same signal used to control the switch 76, or an inverse of that signal.

The value of the threshold Vt can be set in accordance with a minimum voltage required by the regulators 40, 42, and 44 to operate, and in accordance with the expected range of voltages of the primary battery, Vbat, which as noted earlier can range from 1.2 to 3.2V. For example, if these regulators must produce power supplies VDDD, VDDA and VDDF equal to 2.8V, then Vt may be set to a slightly higher voltage of 2.9V. Thus, if 2.9<Vbat<3.2, switch 76 will send Vbat directly to the first circuitry 81 without boosting. The regulators can then drop this voltage to appropriate power supply levels. If 1.2<Vbat<2.9, then switch 76 will send Vbat to the boost converter 64, where it can be boosted to Vbat+, which again may comprise 3.2V or so. The regulators can again drop this boosted voltage Vbat+ to appropriate power supply levels. Using this scheme, and in distinction to the architecture of FIG. 4, the battery voltage, Vbat, is not always boosted before being sent to the regulators, and instead is only boosted when Vbat has dropped below the threshold. Because voltage boosting requires power, selective enablement of the boost converter 64 in this fashion saves power in the IPG 500 compared to prior approaches.

Although not shown, determining the relevant magnitudes of Vbat and Vt and producing an appropriate control signal for the switch 76 can be accomplished in several different ways. Vbat can be digitized at an Analog-to-Digital (A/D) converter and digitally compared to Vt at the digital circuitry 52 to issue an appropriate digital control signal for the switch 76. Alternatively, a comparator comprising part of analog circuitry 50 can receive Vbat and Vt in analog form, which comparator can then issue the digital control signal for the switch 76. Switch 76 can comprise a single transistor, or more-complicated switching circuitry.

In a second difference with the primary-battery architecture of FIG. 4, notice that second circuitry 84—including the telemetry tank circuitry 24 and the DC-DC converter 22 that generates the compliance voltage, V+—receives the battery voltage Vbat directly without boosting from the boost converter 64. This is in recognition that these circuits can operate satisfactorily even at very low levels for Vbat, and therefore that it is unnecessary to expend power boosting the input power supply 86 of those circuits to higher levels. For example, the DC-DC converter 22 already contains circuitry to boost its input voltage, i.e., to V+as necessary to power the DAC(s) 33, and such boosting circuitry within the converter 22 does not require any particular magnitude of the input voltage to function. Tank circuitry 24 can also perform satisfactorily at low levels of Vbat. If Vbat drops to low levels, the strength of transmission of wireless signals from the coil 13 to the external controller 80 (FIG. 2) will be reduced accordingly. However, even if wireless transmissions from the IPG 500 have a reduced signal strength, they will still be capable of receipt at the external controller 80, although perhaps from a smaller distance. In any event, not powering the DC-DC converter 22 and tank circuitry 24 from boost converter 64 once again reduces reliance on the converter 64, which saves power in the IPG 500. Because boost converter 64 is operated in only particular, narrower circumstances, and is used only to power the regulators 40, 42, and 44, the converter 64 need not supply an output Vbat+ with as high of a current capacity.

The architecture of IPG 500 of FIG. 5 results in significant power savings when compared with the architecture of IPG 400 of FIG. 4, which as noted earlier is important in an implantable medical device that uses a primary, non-rechargeable battery. The boost converter 64 operates at an efficiency of about 70%, whereas the regulators 40, 42, and 44 operate at efficiencies at about 90% when reducing the input power supply 88 to form lower power supply voltages VDDA, VDDD, and VDDF. Therefore, when Vbat≥Vt, it is more efficient to allow the regulators to scale down the input power supply voltage 88 than to use the boost converter 64 to provide this voltage.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
    at least one electrode configured to provide stimulation to a patient's tissue;
    a battery configured to output a battery voltage;
    a first converter circuit configured to boost the battery voltage to a first boosted voltage;
    threshold circuitry configured to determine if the battery voltage is greater than or equal to a predetermined threshold voltage, and configured to determine if the battery voltage is less than the predetermined threshold voltage;
    first circuitry powered by the battery voltage when the threshold circuitry determines that the battery voltage is greater than or equal to the predetermined threshold voltage, and by the boosted voltage when the threshold circuitry determines that the battery voltage is less than the predetermined threshold voltage;
    a second converter circuit configured to boost the battery voltage to a second boosted voltage; and
    at least one Digital-to-Analog converter configured to provide current to the at least one electrode, wherein the at least one Digital-to-Analog converter is powered only by the second boosted voltage.

2. The implantable medical device of claim 1, further comprising telemetry circuitry, wherein the telemetry circuitry is powered by the battery voltage.

3. The implantable medical device of claim 1, wherein the first circuitry comprises one or more regulators.

4. The implantable medical device of claim 3, further comprising circuit elements, wherein each of the one or more regulators supplies a constant voltage to power at least one of the circuit elements.

5. The implantable medical device of claim 4, wherein one of the circuit elements is an analog circuit.

6. The implantable medical device of claim 4, wherein one of the circuit elements is a digital circuit.

7. The implantable medical device of claim 1, wherein the predetermined threshold voltage comprises a minimum voltage needed for the first circuitry to operate properly.

8. The implantable medical device of claim 1, further comprising a switch, wherein the switch is controllable by the threshold circuitry to provide the battery voltage to the first circuitry when the battery voltage is greater than or equal to the predetermined threshold voltage, and the switch is controllable to provide the boosted voltage to the first circuitry when the battery voltage is less than the predetermined threshold voltage.

9. The implantable medical device of claim 1, further comprising circuitry configured to monitor a voltage measured at the at least one electrode and to adjust the second boosted voltage in accordance with the voltage monitored at the at least one electrode.

10. The implantable medical device of claim 1, wherein the threshold circuitry is powered by the battery voltage when the threshold circuitry determines that the battery voltage is greater than or equal to the predetermined threshold voltage, and by the boosted voltage when the threshold circuitry determines that the battery voltage is less than the predetermined threshold voltage.

11. The implantable medical device of claim 1, wherein the threshold circuitry comprises a comparator.

12. The implantable medical device of claim 1, further comprising an Analog-to-Digital converter configured to digitize the battery voltage, wherein the threshold circuitry comprises digital circuitry, and wherein the digitized battery voltage is digitally compared to the predetermined threshold voltage in the digital circuitry.

13. An implantable medical device, comprising:
    at least one electrode configured to provide stimulation to a patient's tissue;
    a battery configured to output a battery voltage;
    a first converter circuit configured to boost the battery voltage to a first boosted voltage;
    threshold circuitry configured to determine if the battery voltage is greater than or equal to a predetermined threshold voltage, and configured to determine if the battery voltage is less than the predetermined threshold voltage;
    first circuitry powered by the battery voltage when the threshold circuitry determines that the battery voltage is greater than or equal to the predetermined threshold voltage, and by the boosted voltage when the threshold circuitry determines that the battery voltage is less than the predetermined threshold voltage;
    a second converter circuit configured to boost the battery voltage to a second boosted voltage; and
    at least one third converter circuit configured to provide a stimulation current to the at least one electrode, wherein the at least one third converter circuit is powered by only the second boosted voltage.

14. The implantable medical device of claim 13, wherein the at least one electrode is configured to contact a patient's tissue.

15. The implantable medical device of claim 13, further comprising telemetry circuitry, wherein the telemetry circuitry is powered by the battery voltage.

16. The implantable medical device of claim 13, wherein the first circuitry comprises one or more regulators each configured to supply a constant power supply voltage.

17. The implantable medical device of claim 13, wherein the predetermined threshold voltage comprises a minimum voltage needed for the first circuitry to operate properly.

18. The implantable medical device of claim 13, further comprising a switch, wherein the switch is controllable by the threshold circuitry to provide the battery voltage to the first circuitry when the battery voltage is greater than or equal to the predetermined threshold voltage, and the switch is controllable to provide the boosted voltage to the first circuitry when the battery voltage is less than the predetermined threshold voltage.

19. The implantable medical device of claim 13, wherein the threshold circuitry comprises a comparator.

20. The implantable medical device of claim 13, further comprising an Analog-to-Digital converter configured to digitize the battery voltage, wherein the threshold circuitry comprises digital circuitry, and wherein the digitized battery voltage is digitally compared to the predetermined threshold voltage in the digital circuitry.

\* \* \* \* \*